(12) United States Patent
Marchetti et al.

(10) Patent No.: US 8,314,236 B2
(45) Date of Patent: *Nov. 20, 2012

(54) TRAZODONE AND TRAZODONE HYDROCHLORIDE IN PURIFIED FORM

(75) Inventors: Marcello Marchetti, Rome (IT);
Tommaso Iacoangeli, Rome (IT);
Giovanni Battista Ciottoli, Rome (IT);
Giuseppe Biondi, Castel Gandolfo (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/370,735

(22) Filed: Feb. 10, 2012

(65) Prior Publication Data

US 2012/0142699 A1 Jun. 7, 2012

Related U.S. Application Data

(63) Continuation of application No. 12/513,048, filed as application No. PCT/EP2008/059640 on Jul. 23, 2008, now Pat. No. 8,133,893.

(60) Provisional application No. 60/976,535, filed on Oct. 1, 2007.

(30) Foreign Application Priority Data

Aug. 3, 2007 (IT) .................................. MI07A1603

(51) Int. Cl.
*C07D 471/04* (2006.01)
(52) U.S. Cl. .................................. 544/362; 514/253.04
(58) Field of Classification Search ........................ None
See application file for complete search history.

(56) References Cited

U.S. PATENT DOCUMENTS

2010/0256159 A1   10/2010   Marchetti et al.

*Primary Examiner* — Emily Bernhardt
(74) *Attorney, Agent, or Firm* — Oblon, Spivak, McClelland, Maier & Neustadt, L.L.P.

(57) ABSTRACT

A process of production of trazodone or trazodone hydrochloride that comprises: (a) preparing an organic phase comprising trazodone in at least one organic solvent; (b) preparing an aqueous phase comprising at least one basic compound; (c) mixing said aqueous phase with said organic phase; (d) heating at a temperature of at least 40° C. for at least 30 minutes; (e) recovering said trazodone; and, optionally, (f) treating said trazodone with hydrochloric acid to obtain trazodone hydrochloride. Trazodone or trazodone hydrochloride comprising less than 15 ppm of alkylating substances, and a pharmaceutical composition comprising said trazodone hydrochloride.

20 Claims, No Drawings

TRAZODONE AND TRAZODONE HYDROCHLORIDE IN PURIFIED FORM

CROSS REFERENCES TO RELATED APPLICATIONS

This application is a Continuation of U.S. application Ser. No. 12/513,048, filed on Sep. 21, 2009, which was a 371 of International Patent Application No. PCT/EP08/59640, filed on Jul. 23, 2008, and claims priority to U.S. Provisional Patent Application No. 60/976,535, filed on Oct. 1, 2007, and Italian Patent Application No. MI2007A 001603, filed on Aug. 3, 2007.

FIELD OF THE INVENTION

The present invention relates to a purified form of trazodone and trazodone hydrochloride, and the process for preparation thereof.

In particular the invention relates to a purified form of trazodone and trazodone hydrochloride comprising less than 15 ppm of alkylating substances of proven or suspected genotoxicity.

PRIOR ART

Trazodone, or 2-[3-[4-(3-chlorophenyl)-1-piperazinylpropyl]-1,2,4-triazolo[4,3-a]pyridin-3(2H)-one, is an antidepressant which, though having a significant effect on the serotonin receptors, is neither a psychostimulant, nor a MAO inhibitor, nor a tricyclic antidepressant. Furthermore, trazodone possesses analgesic properties.

Trazodone alleviates the characteristic symptoms of depression, in particular anxiety, somatization, psychomotor retardation, hypochondria, mood swings, irritability, insomnia, apathy, feeling of fatigue and lack of energy, depressed mood.

Trazodone has also proved effective in controlling pronounced essential tremor, probably on account of its serotoninergic activity.

Moreover, the antidepressant and anxiolytic properties of trazodone have proved useful in the treatment of symptoms of withdrawal from cocaine, benzodiazepines and alcohol. Besides the above-mentioned activities, its sleep-inducing activity is also very interesting.

Trazodone is preferably used medically in the form of a pharmaceutically acceptable salt of acid addition. The preferred form is the hydrochloride form obtained by treatment of the free base with hydrochloric acid.

Trazodone hydrochloride is represented by the following structural formula:

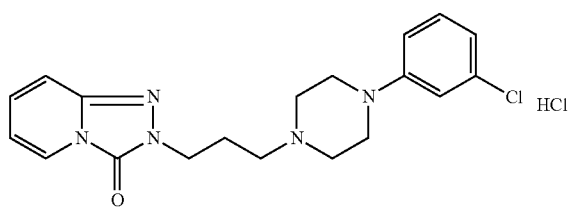

Some economically advantageous methods of preparation of trazodone hydrochloride are described in U.S. Pat. No. 3,381,009 and EP 1,108,722.

A first method comprises reacting s-triazolo-[4,3-a]-pyridin-3-one of formula I with N-(3-chlorophenyl)-N'-(3-chloropropyl)-piperazine of formula II:

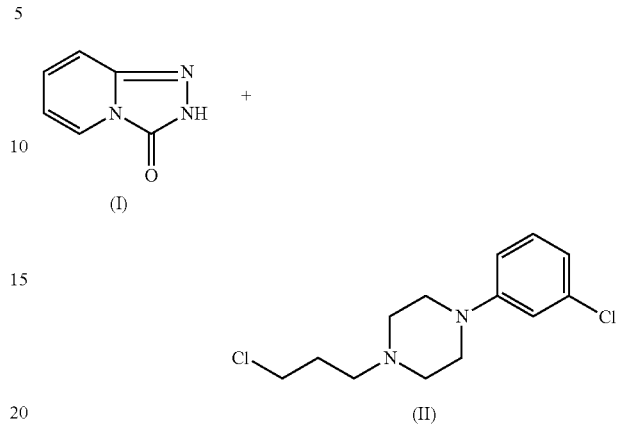

A second method comprises reacting 2-(3-chloropropyl)-s-triazolo-[4,3-a]-pyridin-3-one of formula III with N-(3-chlorophenyl)-piperazine of formula IV:

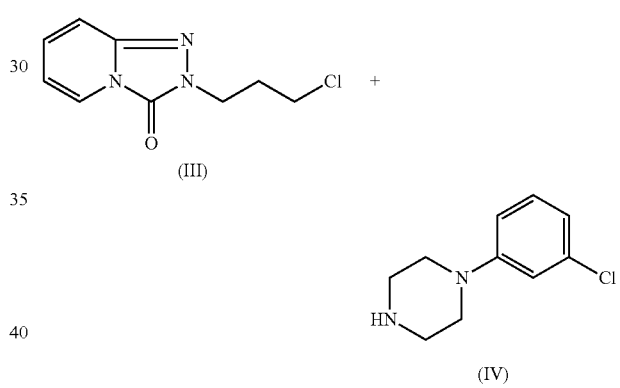

A third method comprises reacting 2-(γ-morpholino-propyl)-s-triazolo-[4,3-a]-pyridin-3-one of formula V with 3-chloroaniline of formula VI

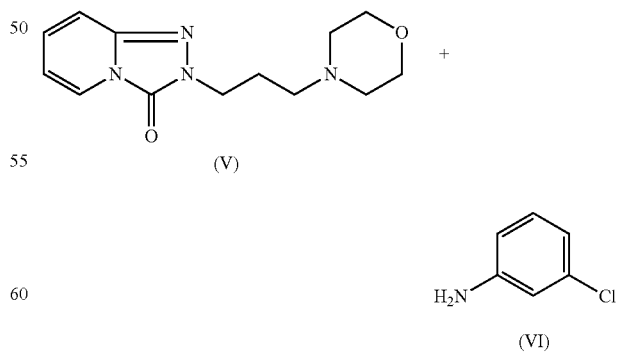

A fourth method comprises reacting 2-(3-aminopropyl)-s-triazolo[4,3-a]-pyridin-3-one of formula VII with 3-chloro-N,N'-dichloroethylaniline of formula VIII:

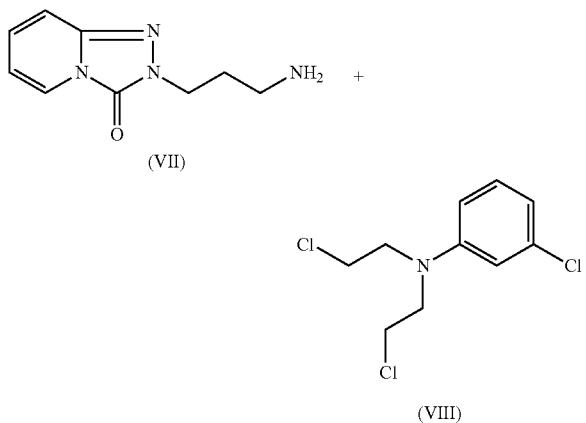

(VII)

(VIII)

A fifth method comprises reacting 2-{3-[bis-(2-chloroethyl)-amino]-propyl}2H-[1,2,4]triazolo[4,3-a]pyridin-3-one of formula IX with 3-chloroaniline of formula VI.

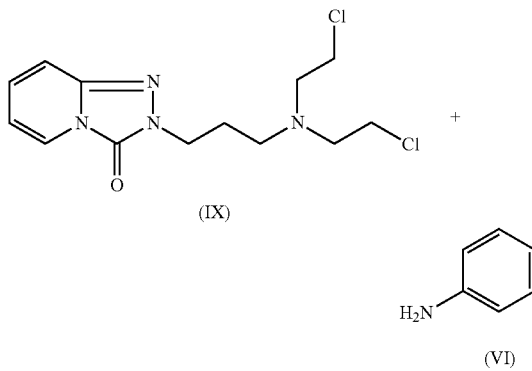

(IX)

(VI)

Once trazodone has been obtained, trazodone hydrochloride is easily obtained by reaction with hydrochloric acid, for example by treating an organic solution of trazodone with an aqueous solution of hydrochloric acid, as described for example in patent EP 1,108,722.

Preparation of the aforementioned intermediates from I to IX requires the use of alkylating substances of proven genotoxicity, such as 2,2-dichloroethylamine, used for obtaining compound IV by reaction with compound VI; 1-bromo-3-chloropropane, used for obtaining compound II by reaction with compound IV.

Compounds II, III, VIII and IX are also alkylating substances and therefore potentially genotoxic. Apart from the aforementioned alkylating substances, in alternative processes for production of trazodone it may be possible to use similar alkylating substances, for example 2,2-dibromoethylamine or 1,3-dichloropropane.

The content of said alkylating substances in the final product, represented by trazodone and trazodone hydrochloride, should be reduced to the least possible amount. In particular, the toxicological threshold for ingestion of these alkylating substances has been determined as 1.5 µg per day.

Therefore, assuming a daily dose of 100 mg of trazodone hydrochloride, the quantity of alkylating substances present as impurities in the product should be less than 15 ppm. If, however, we consider the maximum daily dose of 600 mg of trazodone hydrochloride, the quantity of alkylating substances present as impurities in the product should even be less than 2.5 ppm.

Unfortunately, the processes of preparation described in the aforementioned patents U.S. Pat. No. 3,381,009 and EP 1,108,722 do not allow the content of these alkylating substances to be reduced to below 15 ppm, let alone below 2.5 ppm.

Therefore, the applicant tackled the problem of devising a process for production of trazodone and trazodone hydrochloride that makes it possible to lower the content of these alkylating substances in the final product to below 15 ppm. Moreover, said production process must be economically advantageous and must give high yields of final product.

DEFINITIONS

In the present description and in the claims given later, the expression "trazodone" means trazodone in the form of free base, whereas the expression "trazodone hydrochloride" means the salt formed by the addition of hydrochloric acid to trazodone.

Moreover, in the present description and in the claims given later, the expression "alkylating substances" is used to indicate substances that are capable of introducing an alkyl group in a compound used in the synthesis of trazodone or of an intermediate thereof.

DESCRIPTION OF THE INVENTION

Surprisingly, the applicant found that addition of an aqueous solution comprising a basic compound to a solution of trazodone in an organic solvent reduces the amount of alkylating substances in the final product to below 15 ppm.

Therefore, the present invention relates to a production process of trazodone or of trazodone hydrochloride that comprises the steps of:

(a) preparing an organic phase comprising trazodone in at least one organic solvent;

(b) preparing an aqueous phase comprising at least one basic compound;

(c) mixing said aqueous phase with said organic phase;

(d) heating at a temperature of at least 40° C. for at least 30 minutes;

(e) recovering said trazodone; and, optionally (f) treating said trazodone with hydrochloric acid to obtain trazodone hydrochloride.

The production process of the present invention makes it possible to reduce the amount of alkylating substances in the final product, represented by trazodone or by trazodone hydrochloride, to below 15 ppm, preferably below 10 ppm, and more preferably below 2.5 ppm.

Advantageously, according to a preferred aspect of the present invention, the production process of the present invention makes it possible to reduce the amount of alkylating substances in the final product to below 1 ppm.

The process of the present invention has been shown to be economically advantageous, keeping the yield of the final product above 85%, and preferably above 90%.

Preferably said organic phase is represented by a solution of trazodone in said organic solvent.

Advantageously, said organic solvent can be selected from any organic solvents that are inert with respect to trazodone and that are able to dissolve trazodone.

Preferably, said organic solvent is selected from the group comprising alcohols, for example, ethyl alcohol, propyl alcohol, isobutyl alcohol, hexyl alcohol, and benzyl alcohol; ethers, for example ethyl ether, propyl ether; hydrocarbons, for example toluene, benzene, xylene; ketones, for example acetone, methyl ethyl ketone, methyl isobutyl ketone; esters, for example ethyl acetate. The preferred organic solvent for preparation of the organic phase is isobutyl alcohol.

Preferably, said organic phase comprises an amount of trazodone in the range from 10 g to 50 g per 100 grams of organic phase, more preferably from 20 g to 35 g per 100 grams of organic phase, and even more preferably from 25 g to 30 g per 100 grams of organic phase.

Preferably said aqueous phase is represented by a solution of a basic compound in water.

Advantageously, said aqueous phase comprises at least one basic compound selected from the group comprising at least one inorganic base, at least one organic base, or mixtures thereof.

Useful examples of inorganic bases are sodium hydroxide, potassium hydroxide, sodium carbonate, potassium carbonate, sodium bicarbonate, potassium bicarbonate, sodium phosphate, potassium phosphate, ammonium hydroxide, magnesium oxide, hydrazine, and hydroxylamine.

Useful examples of organic bases are aliphatic or aromatic amines, for example methylamine, ethylamine, propylamine, butylamine, diethylamine, trimethylamine, triethylamine, ethanolamine, diethanolamine, triethanolamine, N,N-dimethylethanolamine, N-methylethanolamine, ethylenediamine, piperidine, quinoline, imidazole, benzimidazole, histidine, pyridine, picoline, lutidine, collidine, morpholine, N-methylmorpholine, benzylamine, and cyclohexylamine.

Preferably, said basic compound is added in an amount in the range from 0.05 to 1 mol per mol of trazodone, more preferably from 0.2 to 0.8 mol per mol of trazodone, and even more preferably from 0.4 to 0.6 mol per mol of trazodone.

Advantageously, said aqueous phase is added in an amount in the range from 30 g to 100 g per 100 grams of organic phase, more preferably from 40 g to 90 g per 100 grams of organic phase, and even more preferably from 50 g to 80 g per 100 grams of organic phase.

Preferably, said aqueous phase comprises a phase transfer catalyst.

Advantageously, said phase transfer catalyst is selected from the group comprising quaternary ammonium salts and quaternary phosphonium salts.

Preferably, said quaternary ammonium salts are selected from the group comprising benzyl tributyl ammonium bromide, benzyl tributyl ammonium chloride, benzyl triethyl ammonium bromide, benzyl triethyl ammonium chloride, benzyl trimethyl ammonium chloride, cetyl pyridinium bromide, cetyl pyridinium chloride, cetyl trimethyl ammonium bromide, didecyl dimethyl ammonium chloride, dodecyl trimethyl ammonium bromide, dodecyl trimethyl ammonium chloride, methyl tributyl ammonium chloride, methyl tributyl ammonium hydrogen sulphate, methyl tricaprilyl ammonium chloride, methyl trioctyl ammonium chloride, phenyl trimethyl ammonium chloride, tetrabutyl ammonium borohydride, tetrabutyl ammonium bromide, tetrabutyl ammonium chloride, tetrabutyl ammonium fluoride, tetra butyl ammonium hydrogen sulphate, tetrabutyl ammonium hydroxide, tetrabutyl ammonium iodide, tetrabutyl ammonium perchlorate, tetraethyl ammonium bromide, tetraethyl ammonium chloride, tetraethyl ammonium hydroxide, tetrahexyl ammonium bromide, tetrahexyl ammonium iodide, tetramethyl ammonium bromide, tetramethyl ammonium chloride, tetramethyl ammonium fluoride, tetramethyl ammonium hydroxide, tetramethyl ammonium iodide, tetraoctyl ammonium bromide, tetrapropyl ammonium bromide, tetrapropyl ammonium chloride, tetrapropyl ammonium hydroxide, tributyl methyl ammonium chloride, triethyl benzyl ammonium chloride.

Advantageously, said quaternary ammonium salts are selected from the group comprising tetrabutyl ammonium bromide, tetrabutyl ammonium chloride, benzyl triethyl ammonium bromide, benzyl triethyl ammonium chloride, benzyl trimethyl ammonium chloride, benzyl trimethyl ammonium bromide, benzyl tributyl ammonium bromide, and benzyl tributyl ammonium chloride.

The series of phase transfer catalysts Aliquat® produced and marketed by the company Cognis Corp., Tucson, Ariz. can be used advantageously in the production process of the present invention. Preferred examples are Aliquat® 100, Aliquat® 134, Aliquat® 175, and Aliquat® 336.

Preferably, said quaternary phosphonium salts are selected from the group comprising benzyl triphenyl phosphonium bromide, benzyl triphenyl phosphonium chloride, butyl triphenyl phosphonium bromide, butyl triphenyl phosphonium chloride, ethyl triphenyl phosphonium acetate, ethyl triphenyl phosphonium bromide, ethyl triphenyl phosphonium iodide, hexadecyl tributyl phosphonium bromide, methyl triphenyl phosphonium bromide, tetrabutyl phosphonium bromide, and tetraphenyl phosphonium bromide.

Preferably, said aqueous phase comprises an amount of phase transfer catalyst in the range from 0.05 g to 0.5 g per 100 grams of aqueous phase, more preferably from 0.1 g to 0.3 g per 100 grams of aqueous phase, and even more preferably from 0.15 g to 0.2 g per 100 grams of aqueous phase.

Preferably, said heating step (d) is carried out at a temperature between 40° and the boiling point of the mixture of organic phase and aqueous phase, for a period of time between 30 minutes and 300 minutes, preferably between 60 and 240 minutes, more preferably between 90 and 180 minutes.

Preferably, the recovery step (e) is carried out by separating the aqueous phase from the organic phase comprising the trazodone, and cooling the latter to a temperature below 30° C., preferably below 20° C., and even more preferably below 10° C., to promote the crystallization and precipitation of trazodone, which is finally separated, for example by filtration.

Advantageously, in the final treatment step (f), the trazodone is preferably dissolved in a suitable organic solvent, selected, for example, from those stated previously for the preparation of the organic phase. The solvent preferred in this step is acetone. The solution thus obtained is treated with an aqueous solution of hydrochloric acid as described in patent EP 1,108,722. The precipitate of trazodone hydrochloride is then filtered, washed, and dried according to the conventional techniques known by a person skilled in the art.

The trazodone and the trazodone hydrochloride obtained by the process of the present invention are characterized by a content of alkylating substances, of proven or suspected genotoxicity, below 15 ppm.

Depending on the production process selected for the production of trazodone and of trazodone hydrochloride, the alkylating substances present as impurities are, for example, 2,2-dichloromethylamine, 1-bromo-3-chloro-propane, N-(3-chlorophenyl)-N'-(3-chloropropyl)-piperazine (formula II), 2-(3-chloropropyl)-s-triazolo-[4,3-a]-pyridin-3-one (formula III), 3-chloro-N,N'-dichloroethyl-aniline (formula VIII), 2-{3-[bis-(2-chloroethyl)-amino]-propyl}-2H-[1,2,4]triazolo[4,3-a]pyridin-3-one (formula IX), 2,2-dibromoethylamine, and 1,3-dichloropropane.

In particular, the alkylating substances encountered most frequently are represented by 2,2-dichloroethylamine, 1-bromo-3-chloro-propane, and N-(3-chlorophenyl)-N'-(3-chloropropyl)-piperazine.

2,2-Dichloroethylamine (CAS No. 334-22-5) and 1-bromo-3-chloro-propane (CAS No. 109-70-6) are known genotoxic substances as reported in TOXNET, a database published by the National Library of Medicine, US on the website http://toxnet.nlm.nih.gov/.

The genotoxic activity of N-(3-chlorophenyl)-N'-(3-chloropropyl)-piperazine has been assessed on histidine-dependent auxotrophic mutants of *Salmonella typhimurium* strains TA1535, TA1537, TA 98 and TA100, and on tryptophan-dependent mutants of *Escherichia coli* strain WP2 uvrA (pKM101), exposed to a solution of N-(3-chlorophenyl)-N'-(3-chloropropyl)-piperazine in dimethylsulphoxide (DMSO) and using DMSO as negative control. Two independent mutation tests were performed, both in the presence and absence of a liver microsomal fraction (S9 mix) of rat treated with phenobarbital and 5,6-benzoflavone. Tests were standard plate incorporation assays and performed according to the current regulatory guidelines. A substantial increase in reversion to prototrophy was obtained on strain TA1535 in the presence of S9 mix. In the two assays the increase was concentration related and reached, following exposure to 1500 µg per plate of N-(3-chlorophenyl)-N'-(3-chloropropyl)-piperazine, 6.4 and 5.1 times the control value. It was therefore concluded that N-(3-chlorophenyl)-N'-(3-chloropropyl)-piperazine exhibited genotoxic activity in said bacterial system following metabolic activation.

Surprisingly, the total content of said alkylating substances in the trazodone or in the trazodone hydrochloride obtained using the process of the present invention was below 15 ppm, preferably less than 10 ppm, and even more preferably less than 2.5 ppm. In the preferred embodiment, the content of each of said alkylating substances in the trazodone or in the trazodone hydrochloride obtained using the process of the present invention was below 1 ppm.

Therefore, the present invention also relates to trazodone or trazodone hydrochloride comprising less than 15 ppm of alkylating substances, preferably less than 10 ppm, and even more preferably less than 2.5 ppm.

In a preferred embodiment, the present invention also relates to trazodone or trazodone hydrochloride comprising less than 1 ppm, and preferably less than 0.5 ppm, of each alkylating substance.

Preferably said alkylating substances are selected from the group comprising 2,2-dichloroethylamine, 1-bromo-3-chloro-propane; and N-(3-chloro-phenyl)-N'-(3-chloropropyl)-piperazine (formula II), 2-(3-chloropropyl)-s-triazolo-[4,3-a]-pyridin-3-one (formula III), 3-chloro-N,N'-dichloroethyl-aniline (formula VIII), 2-{3-[bis-(2-chloroethyl)-amino]-propyl}-2H-[1,2,4]triazolo[4,3-a] pyridin-3-one (formula IX), 2,2-dibromoethylamine, and 1,3-dichloro-propane.

Even more preferably said alkylating substances are selected from the group comprising 2,2-dichloroethylamine, 1-bromo-3-chloropropane, and N-(3-chlorophenyl)-N'-(3-chloropropyl)-piperazine.

The trazodone hydrochloride of the present invention can be used advantageously in the preparation of pharmaceutical compositions mixed with at least one pharmaceutically acceptable excipient.

Thus, the present invention also relates to a pharmaceutical composition comprising the trazodone hydrochloride of the present invention as described previously together with at least one pharmaceutically acceptable excipient.

The term "pharmaceutically acceptable excipient" means, without particular limitations, any material suitable for the preparation of a pharmaceutical composition that is to be administered to a living being.

Such materials, known by a person skilled in the art, are for example antiadherents, binders, disintegrants, fillers, diluents, flavouring agents, colorants, fluidizers, lubricants, preservatives, moistening agents, absorbents, and sweeteners.

Useful examples of pharmaceutically acceptable excipients are sugars, such as lactose, glucose or sucrose, starches, such as maize starch, and potato starch, cellulose and derivatives thereof, such as sodium carboxymethylcellulose, ethylcellulose, and cellulose acetate, gum tragacanth, malt, gelatin, talc, cocoa butter, waxes, oils, such as peanut oil, cottonseed oil, safflower oil, sesame oil, olive oil, maize oil, and soya oil, glycols such as propylene glycols, polyols, such as glycerol, sorbitol, mannitol, and polyethylene glycol, esters, such as ethyl oleate, and ethyl laurate, agar-agar, buffers, such as magnesium hydroxide, and aluminium hydroxide, alginic acid, water, isotonic solutions, ethanol, buffer solutions, polyesters, polycarbonates, polyanhydrides, and so on.

The pharmaceutical composition of the present invention can be represented by any composition that can be used for administration of the trazodone hydrochloride of the present invention, preferably compositions for oral or parenteral administration, for example tablets, lozenges, capsules, solutions, suspensions, dispersions, and syrups.

The invention is illustrated by the following examples, though without limiting it.

EXAMPLE 1

Preparation in the Presence of a Strong Base (NaOH)

37.1 g of trazodone (equal to about 0.100 mol) obtained according to example 1 of U.S. Pat. No. 3,381,009 was put in a 500-ml flask together with 140 ml of isobutyl alcohol. Then 100 ml of an aqueous solution of NaOH at 2% was added, and the resultant mixture was heated to about 80° C. and held at this temperature, with stirring, for about 3 hours.

Then the organic phase was separated from the aqueous phase and then washed with water. The residual water present in the organic phase was removed by azeotropic distillation. The resultant solution was cooled to 5° C. to precipitate the crystals of trazodone base, which were separated by filtration.

The wet product (about 40 g) was dissolved in about 270 ml of acetone, heated until dissolution occurred, and then 12N HCl aqueous solution was added to the solution up to pH between 3 and 4 to salify the trazodone base and obtain the corresponding hydrochloride.

The resultant solution was cooled to 5° C. to precipitate the crystals of trazodone hydrochloride. The trazodone hydrochloride thus obtained was filtered, washed with acetone and dried at reduced pressure. At the end of drying, 35.5 g of trazodone hydrochloride was obtained (equal to about 0.087 mol), at a product yield equal to about 87%.

TABLE 1

| | Alkylating substances | | |
|---|---|---|---|
| | 2,2-dichloroethylamine | 1-bromo-3-chloro-propane | N-(3-chlorophenyl)-N'-(3-chloropropyl)-piperazine |
| Initial content (ppm) | 10 | 15 | 50 |
| Final content (ppm) | <0.46 | <0.2 | <0.04 |

EXAMPLE 2

Preparation in the Presence of Weak Base ($Na_2CO_3$)

37.1 g of trazodone (equal to about 0.100 mol) obtained according to example 1 of U.S. Pat. No. 3,381,009 was put in a 500-ml flask together with 140 ml of isobutyl alcohol. Then 100 ml of an aqueous solution containing 5.3 g of $Na_2CO_3$ was added, and the resultant mixture was heated to about 80° C. and left at this temperature, with stirring, for about 4 hours.

Then the organic phase was separated from the aqueous phase and then washed with water. The residual water present in the organic phase was removed by azeotropic distillation. The resultant solution was cooled to 5° C. to precipitate the crystals of trazodone base, which were separated by filtration.

The wet product (about 42 g) was dissolved in about 270 ml of acetone, heated until dissolution occurred, and then a 12N HCl aqueous solution was added to the solution until the pH was between 3 and 4 to salify the trazodone base and obtain the corresponding hydrochloride.

The resultant solution was cooled to 5° C. to precipitate the crystals of trazodone hydrochloride. The trazodone hydrochloride thus obtained was filtered, washed with acetone and dried at reduced pressure. At the end of drying, 37.0 g of trazodone hydrochloride was obtained (equal to about 0.091 mol), at a product yield equal to about 91%.

TABLE 2

| | Alkylating substances | | |
|---|---|---|---|
| | 2,2-dichloroethylamine | 1-bromo-3-chloro-propane | N-(3-chlorophenyl)-N'-(3-chloropropyl)-piperazine |
| Initial content (ppm) | 5 | 20 | 35 |
| Final content (ppm) | <0.46 | <0.2 | <0.4 |

EXAMPLE 3

Preparation in the Presence of Weak Base ($Na_2CO_3$) and Phase Transfer Catalyst (Benzyltriethylammonium Chloride)

37.1 g of trazodone (equal to about 0.100 mol) obtained according to example 1 of U.S. Pat. No. 3,381,009 was put in a 500-ml flask together with 140 ml of isobutyl alcohol. Then 100 ml of an aqueous solution containing 5.3 g of $Na_2CO_3$ and 150 mg of benzyltriethylammonium chloride was added, and the resultant mixture was heated to about 80° C. and left at this temperature, with stirring, for about 2 hours.

Then the organic phase was separated from the aqueous phase and then washed with water. The residual water present in the organic phase was removed by azeotropic distillation. The resultant solution was cooled to 5° C. to precipitate the crystals of trazodone base, which were separated by filtration.

The wet product (about 38.5 g) was dissolved in about 270 ml of acetone, heated until dissolution occurred, and then a 12N HCl aqueous solution was added to the solution until the pH was between 3 and 4 to salify the trazodone base and obtain the corresponding hydrochloride.

The resultant solution was cooled to 5° C. to precipitate the crystals of trazodone hydrochloride. The trazodone hydrochloride thus obtained was filtered, washed with acetone and dried at reduced pressure. At the end of drying, 36.7 g of trazodone hydrochloride was obtained (equal to about 0.090 mol), at a product yield equal to about 90%.

TABLE 3

| | Alkylating substances | | |
|---|---|---|---|
| | 2,2-dichloroethylamine | 1-bromo-3-chloro-propane | N-(3-chlorophenyl)-N'-(3-chloropropyl)-piperazine |
| Initial content (ppm) | 5 | 20 | 35 |
| Final content (ppm) | <0.46 | <0.2 | <0.04 |

EXAMPLE 4

Preparation in the Presence of Strong Base (KOH)

37.1 g of trazodone (equal to about 0.100 mol) obtained according to example 1 of U.S. Pat. No. 3,381,009 was put in a 500-ml flask together with 140 ml of methylisobutyl ketone. Then 100 ml of an aqueous solution containing 2.8 g of KOH was added, and the resultant mixture was heated to about 80° C. and left at this temperature, with stirring, for about 3 hours.

Then the organic phase was separated from the aqueous phase and then washed with water. The residual water present in the organic phase was removed by azeotropic distillation. The resultant solution was cooled to 5° C. to precipitate the crystals of trazodone base, which were separated by filtration.

The wet product (about 38 g) was dissolved in about 270 ml of acetone, heated until dissolution occurred, and then a 12N HCl aqueous solution was added to the solution until the pH was between 3 and 4 to salify the trazodone base and obtain the corresponding hydrochloride.

The resultant solution was cooled to 5° C. to precipitate the crystals of trazodone hydrochloride. The trazodone hydrochloride thus obtained was filtered, washed with acetone and dried at reduced pressure. At the end of drying, 35.5 g of trazodone hydrochloride was obtained (equal to about 0.087 mol), at a product yield equal to about 87%.

TABLE 4

| | Alkylating substances | | |
|---|---|---|---|
| | 2,2-dichloroethylamine | 1-bromo-3-chloro-propane | N-(3-chlorophenyl)-N'-(3-chloropropyl)-piperazine |
| Initial content (ppm) | 7 | 10 | 50 |
| Final content (ppm) | <0.46 | <0.2 | <0.4 |

The initial and final content of the alkylating substances shown in the above Tables 1 to 4 was determined according to the following procedures.

Assay for the Determination of 2,2-Dichloroethylamine in Trazodone Hydrochloride by UV/Vis Spectrophotometry The assay is based on the reaction of 2,2-dichloroethylamine with 4-(4-nitrobenzyl)-pyridine according to a modified Friedman-Boger procedure as described in Anal. Chem. 33, 906-910, 1961, "Colorimetric estimation of nitrogen mustards in aqueous media".

Briefly, a solution of 4-(4-nitrobenzyl)pyridine in acetone was added to an aqueous solution of trazodone hydrochloride (0.25 g/ml). The resultant mixture was heated to 100° C. for 20 minutes, and then quickly cooled on an ice bath. 1 ml of acetone and 3 ml of 1N sodium hydroxide were added to the solution. The coloured derivative was then extracted in chloroform (3 ml). The absorbance value at 544 nm was recorded against a blank sample, and the second derivative ($\delta$) was calculated from the value obtained. The content, in ppm, of 2,2-dichloroethylamine in the trazodone hydrochloride was found by using the external standard method.

The reaction was specific for 2,2-dichloroethylamine as no coloured derivative was obtained in the conditions described for other alkylating agents such as 1-bromo-3-chloropropane and N-(3-chlorophenyl)-N'-(3-chloropropyl)-piperazine.

Linearity was verified from 1 to 10 ppm of 2,2-dichloroethylamine. The accuracy of the calibrators was always between 85 and 115% of the theoretical value.

The lower limit of quantification (LLOQ) was set at 1 ppm based on the values of precision (measured as standard deviation, a) of the blank, as follows: $\delta_{LLOQ}=\delta_{blank}+10*\sigma=0.00048+10*0.00024=0.00288$ corresponding to 1.1 ppm.

The limit of detection (LOD) was set at 0.46 ppm, based on the values of precision (measured as standard deviation, $\sigma$) of the blank, as follows: $\delta_{LLOQ}=\delta_{blank}+3*\sigma=0.00048+10*0.00024=0.00288$ corresponding to 0.46 ppm.

The precision was evaluated by calculating the coefficient of variation (CV %) of six determinations. The CV % at 5 ppm was equal to 12.2% and at 10 ppm it was equal to 11.2%.

Assay for the Determination of 1-Bromo-3-Chloropropane in Trazodone Hydrochloride by the Headspace Technique The trazodone hydrochloride was dissolved in a water/methanol solution. After complete dissolution, the solution was put in a headspace autosampler and the content of 1-bromo-3-chloropropane was determined by gas chromatography using a capillary column of medium polarity. The column effluent was monitored using a flame ionization detector. The content of 1-bromo-3-chloropropane was determined as assay limit relative to a standard sample with known content (2 ppm).

| Chromatography conditions | |
|---|---|
| Gas chromatograph | Trace Ultra |
| Analytical column | Capillary column, L = 30 m, inside diameter 0.53 mm, 3 µm (RTX 1301 or equivalent) |
| Stationary phase | 6% cyanopropylphenyl, 94% dimethyl polysiloxane |
| Oven temperature | 90° C. per 2 min then increased to 130° C. at 10° C./min and maintained at 130° C. for 1 min |
| Mobile phase (pressure) | Nitrogen (100 kPa) |
| Detector | FID (air 350 kPa, hydrogen 35 kPa) |
| Retention time | Approx. 3.5 min for 1-bromo-3-chloropropane |
| Run time | 7 min |
| Injector temperature | 250° C. |
| Detector temperature | 250° C. |
| Hydrogen pressure | 35 kPa |
| Air pressure | 350 kPa |

| Conditions for the autosampler | |
|---|---|
| Headspace autosampler | Perkin Elmer TurboMatrix 40 |
| Operating mode | continuous |
| Diameter of transfer tube | 0.25 mm |
| Sample temperature | 90° C. |
| Needle temperature | 150° C. |
| Temperature of transfer tube | 170° C. |
| Time for thermostatic control | 15 minutes |
| Pressurization time | 1 minute |

100 mg of trazodone hydrochloride was accurately weighed in a 22-ml test tube, then an aqueous solution of methanol at 0.025% (v/v) was added. The test tube was sealed with an aluminium crimp cap and PTFE coated butyl rubber septum and was then put in the headspace autosampler.

Linearity was verified from 0.2 to 9.3 ppm of 1-bromo-3-chloropropane, obtaining a correlation coefficient equal to 0.992 (by least squares regression analysis).

The limits of detection (LOD) and the lower limit of quantification (LLOQ) were obtained from the signal/noise ratio (S/N) as follows:

LOD=3×S/N=0.2 ppm

LLOQ=10×S/N=0.5 ppm

The precision, determined on the basis of six repeat determinations, was found to be equal to 3.6% (CV) at 0.5 ppm.

The accuracy was determined as recovery %. Within the range of linearity it was always 100% with reference to the theoretical concentration.

Assay for the Determination of 1-(3-Chlorophenyl)-4-(3-Chloropropyl)Piperazine (CCP) in Trazodone Hydrochloride by High-Performance Liquid Chromatography Coupled to Tandem Mass Spectrometry (HPLC/MS/MS).

The trazodone hydrochloride was dissolved in water and injected into the analyser. Chromatographic separation was obtained using a reversed-phase analytical column of the alkyl amide type.

The eluate from the column was monitored by positive-ion mass spectrometry using the "Multiple Reaction Monitoring" (MRM) technique.

| Chromatography conditions | |
|---|---|
| HPLC system | Agilent series 1200 (or equivalent) |
| Analytical column | ABZ Plus, 75 × 4.6 mm, 3 µm (Supelco) |
| Oven temperature | 40° C. |
| Solvent A | Methanol |
| Solvent B | ammonium acetate 5 mM + 0.1% (v/v) formic acid |
| Operational flow rate | 2 ml/min, a split was used to reduce the flow at the ion source to 0.3 ml/min |
| Elution | Isocratic Solvent A/B = 12/88 (v/v) 3 min |
| Purge | Isocratic Solvent A/B = 80/20 (v/v) 5 min |
| Injection volume | 5 µl |
| Retention time | Approx. 2.5 min for CCP |
| Run time | 10.0 min |

| Mass spectrometry conditions; | |
|---|---|
| Mass spectrometer | Sciex API3000 LC/MS/MS |
| Source | Turbo Ion Spray ® |
| Mode | Positive-ion |
| Detection | Multiple Reaction Monitoring (MRM) |
| Resolution | Q1 low resolution (mass = 273.1 amu), Q3 unit resolution (mass = 154.1 amu). |

Linearity was verified from 0.4 to 8 ppm of 1-(3-chlorophenyl)-4-(3-chloropropyl)piperazine, obtaining a correlation coefficient equal to 0.9987 (by least squares regression analysis).

The accuracy was always between 85% and 115% of the theoretical value.

The lower limit of quantification (LLOQ) was set at 0.4 ppm based on the values of accuracy (85%) and precision (CV=6.7%) obtained from six determinations.

The limit of detection (LOD) was set at 0.04 ppm based on the value of the signal/noise ratio (S/N): LOD=3×S/N=0.04 ppm.

The invention claimed is:

1. A process for producing trazodone or trazodone hydrochloride, which comprises:
   (a) preparing an organic phase comprising trazodone in at least one organic solvent;
   (b) preparing an aqueous phase comprising at least one basic compound;
   (c) mixing said aqueous phase with said organic phase to obtain a mixture;
   (d) heating said mixture at a temperature of at least 40° C. for at least 30 minutes;
   (e) recovering said trazodone; and, optionally,
   (f) treating said trazodone with hydrochloric acid to obtain trazodone hydrochloride.

2. A process according to claim 1, wherein said trazodone or trazodone hydrochloride comprises alkylating substances in a total amount which is less than 15 ppm and said alkylating substances are selected from the group consisting of 2,2-dichloroethylamine, 1-bromo-3-chloro-propane, N-(3-chlorophenyl)-N'-(3-chloropropyl)-piperazine, and a mixture thereof.

3. A process according to claim 2, wherein said trazodone or trazodone hydrochloride comprises less than 10 ppm of said alkylating substances.

4. A process according to claim 2, wherein said trazodone or trazodone hydrochloride comprises less than 2.5 ppm of said alkylating substances.

5. A process according to claim 2, wherein said trazodone or trazodone hydrochloride comprises less than 1 ppm of said alkylating substances.

6. A process according to claim 1, wherein said organic solvent is selected from the group consisting of an alcohol, an ether, a hydrocarbon, a ketone, and an ester.

7. A process according to claim 6, wherein said organic solvent is selected from the group consisting of ethyl alcohol, propyl alcohol, isobutyl alcohol, hexyl alcohol, benzyl alcohol, ethyl ether, propyl ether, toluene, benzene, xylene, acetone, methyl ethyl ketone, methyl isobutyl ketone, and ethyl acetate.

8. A process according to claim 1, wherein said organic phase comprises an amount of trazodone in the range from 10 g to 50 g per 100 grams of organic phase.

9. A process according to claim 1, wherein said aqueous phase comprises at least one basic compound selected from the group consisting of at least one inorganic base, at least one organic base, and a mixture thereof.

10. A process according to claim 9, wherein said inorganic base is selected from the group consisting of sodium hydroxide, potassium hydroxide, sodium carbonate, potassium carbonate, sodium bicarbonate, potassium bicarbonate, sodium phosphate, potassium phosphate, ammonium hydroxide, magnesium oxide, hydrazine, and hydroxylamine.

11. A process according to claim 9, wherein said organic base is selected from the group consisting of an aliphatic amine and an aromatic amine.

12. A process according to claim 1, wherein said basic compound is added in an amount in the range from 0.05 to 1 mol per mole of trazodone.

13. A process according to claim 1, wherein said aqueous phase is added in an amount in the range from 30 g to 100 g per 100 grams of organic phase.

14. A process according to claim 1, wherein said aqueous phase comprises a phase transfer catalyst.

15. A process according to claim 14, wherein said phase transfer catalyst is selected from the group consisting of a quaternary ammonium salt and a quaternary phosphonium salt.

16. A process according to claim 15, wherein said quaternary ammonium salt is selected from the group consisting of benzyl tributyl ammonium bromide, benzyl tributyl ammonium chloride, benzyl triethyl ammonium bromide, benzyl triethyl ammonium chloride, benzyl trimethyl ammonium chloride, cetyl pyridinium bromide, cetyl pyridinium chloride, cetyl trimethyl ammonium bromide, didecyl dimethyl ammonium chloride, dodecyl trimethyl ammonium bromide, dodecyl trimethyl ammonium chloride, methyl tributyl ammonium chloride, methyl tributyl ammonium hydrogen sulphate, methyl tricaprilyl ammonium chloride, methyl trioctyl ammonium chloride, phenyl trimethyl ammonium chloride, tetrabutyl ammonium borohydride, tetrabutyl ammonium bromide, tetrabutyl ammonium chloride, tetrabutyl ammonium fluoride, tetrabutyl ammonium hydrogen sulphate, tetrabutyl ammonium hydroxide, tetrabutyl ammonium iodide, tetrabutyl ammonium perchlorate, tetraethyl ammonium bromide, tetraethyl ammonium chloride, tetraethyl ammonium hydroxide, tetrahexyl ammonium bromide, tetrahexyl ammonium iodide, tetramethyl ammonium bromide, tetramethyl ammonium chloride, tetramethyl ammonium fluoride, tetramethyl ammonium hydroxide, tetramethyl ammonium iodide, tetraoctyl ammonium bromide, tetrapropyl ammonium bromide, tetrapropyl ammonium chloride, tetrapropyl ammonium hydroxide, tributyl methyl ammonium chloride, and triethyl benzyl ammonium chloride.

17. A process according to claim 15, wherein said quaternary ammonium salt is selected from the group consisting of tetrabutyl ammonium bromide, tetrabutyl ammonium chloride, benzyl triethyl ammonium bromide, benzyl triethyl ammonium chloride, benzyl trimethyl ammonium chloride, benzyl trimethyl ammonium bromide, benzyl tributyl ammonium bromide, and benzyl tributyl ammonium chloride.

18. A process according to claim 15, wherein said quaternary phosphonium salt is selected from the group consisting of benzyl triphenyl phosphonium bromide, benzyl triphenyl phosphonium chloride, butyl triphenyl phosphonium bromide, butyl triphenyl phosphonium chloride, ethyl triphenyl phosphonium acetate, ethyl triphenyl phosphonium bromide, ethyl triphenyl phosphonium iodide, hexadecyl tributyl phosphonium bromide, methyl triphenyl phosphonium bromide, tetrabutyl phosphonium bromide, and tetraphenyl phosphonium bromide.

19. A process according to claim 15, wherein said aqueous phase comprises an amount of phase transfer catalyst in the range from 0.05 g to 0.5 g per 100 grams of aqueous phase.

20. A process according to claim 1, wherein said heating (d) is carried out at a temperature between 40° C. and the boiling point of the mixture of organic phase and aqueous phase, for a period of time between 30 minutes and 300 minutes.

* * * * *